US007637866B2

(12) United States Patent
Ono

(10) Patent No.: US 7,637,866 B2
(45) Date of Patent: Dec. 29, 2009

(54) OPTICAL ADAPTOR FOR ENDOSCOPE AND ENDOSCOPE APPARATUS

(75) Inventor: Mitsunobu Ono, Tokyo (JP)

(73) Assignee: Olympus Corporation (JP)

( * ) Notice: Subject to any disclaimer, the term of this patent is extended or adjusted under 35 U.S.C. 154(b) by 667 days.

(21) Appl. No.: 11/129,792

(22) Filed: May 16, 2005

(65) Prior Publication Data

US 2006/0069309 A1 Mar. 30, 2006

(30) Foreign Application Priority Data

May 21, 2004 (JP) ............................. 2004-152467

(51) Int. Cl.
*A61B 1/00* (2006.01)
(52) U.S. Cl. ..................... 600/134; 600/129; 600/172; 361/212
(58) Field of Classification Search ................ 600/129, 600/160, 172, 175, 178, 179, 134; 362/574; 361/212
See application file for complete search history.

(56) References Cited

U.S. PATENT DOCUMENTS

| 3,887,819 | A | * | 6/1975 | Kurasawa | 307/10.1 |
|---|---|---|---|---|---|
| 6,054,716 | A | * | 4/2000 | Sonobe et al. | 250/552 |
| 6,084,252 | A | * | 7/2000 | Isokawa et al. | 257/98 |
| 6,095,970 | A | * | 8/2000 | Hidaka et al. | 600/110 |
| 6,164,208 | A | * | 12/2000 | Hsu et al. | 102/202.5 |
| 6,348,035 | B1 | * | 2/2002 | Takami | 600/132 |
| 6,414,779 | B1 | * | 7/2002 | Mandella et al. | 359/212 |
| 6,661,032 | B2 | * | 12/2003 | Meng et al. | 257/99 |
| 6,796,939 | B1 | * | 9/2004 | Hirata et al. | 600/179 |
| 6,839,097 | B2 | * | 1/2005 | Park et al. | 349/40 |
| 6,861,677 | B2 | * | 3/2005 | Chen | 257/99 |
| 7,140,893 | B2 | * | 11/2006 | Abe et al. | 439/144 |
| 2003/0075987 | A1 | * | 4/2003 | Shields | 307/121 |
| 2003/0122139 | A1 | * | 7/2003 | Meng et al. | 257/81 |
| 2003/0189201 | A1 | * | 10/2003 | Chen | 257/13 |
| 2003/0191369 | A1 | * | 10/2003 | Arai et al. | 600/173 |
| 2004/0092793 | A1 | * | 5/2004 | Akai | 600/134 |
| 2004/0143162 | A1 | * | 7/2004 | Krattiger et al. | 600/175 |

FOREIGN PATENT DOCUMENTS

| JP | 2000-092479 | 3/2000 |
|---|---|---|
| JP | 2002-095624 | 4/2002 |

* cited by examiner

*Primary Examiner*—Linda C Dvorak
*Assistant Examiner*—Samuel Candler
(74) *Attorney, Agent, or Firm*—Ostrolenk Faber LLP

(57) ABSTRACT

An optical adaptor for endoscope according to the present invention includes, in an outer casing, a light emitter, serving as a light source for illumination, and two terminals connected to the positive and negative electrodes of the light emitters to be externally projected from the inside of the outer casing. The connection of a diode between the positive and negative electrodes of the light emitters prevents the static electricity from being applied to the light emitter.

12 Claims, 7 Drawing Sheets

OPTICAL ADAPTOR FOR ENDOSCOPE AND ENDOSCOPE APPARATUS

This application claims benefit of Japanese Application No. 2004-152467 filed in Japan on May 21, 2004, the contents of which are incorporated by this reference.

BACKGROUND OF THE INVENTION

1. Field of the Invention

The present invention relates to an optical adaptor for endoscope which is detachable to a distal part of an endoscope insertion portion and an endoscope apparatus.

2. Description of the Related Art

It is well-known that an endoscope has widely been used in the medical and industrial fields. The endoscope for medical field observes the organ in the body cavity by inserting an elongated insertion unit into the body cavity, and performs various treatments by using a treatment tool inserted in a treatment tool channel if necessary.

Further, in the industrial field, the endoscope observes and treats the scratch or corrosion of a jet engine or a tube of a power plant by inserting an elongated insertion unit thereto.

A bending portion is arranged at the distal end of the endoscope insertion portion and an endoscope operation portion is operated to bend the bending portion, thereby changing the observing direction of an objective at a distal part of an observation optical system arranged in the endoscope insertion portion.

An illumination optical system for illuminating an inspection part observed by the objective at the distal part of the observation optical system is arranged at the bending portion and the distal part of the endoscope insertion portion. It is well-known that a plurality of light-emission diodes (hereinafter, referred to as LEDs) are used for illumination of the illumination optical system and is put into practical use.

Incidentally, the LED has excessively weak property to the static electricity. Therefore, there has been a problem that in applying an electrostatic voltage between the anode and the cathode of the LED, serving as the positive and negative electrodes of the LED, the LED is broken due to the static electricity.

In consideration of the above-mentioned problem, Japanese Unexamined Patent Application Publication No. 2002-95624 discloses a technology for preventing the electrostatic break of the LED due to applying an electrostatic voltage between both the anode and the cathode of the LED by connecting an electrostatic protecting circuit comprising an inductor, capacitor, and a diode between the anode and the cathode of the LED.

Further, Japanese Unexamined Patent Application Publication No. 2000-92479 discloses a technology for preventing the electrostatic break of a power supply circuit due to applying an electrostatic voltage with a simple circuit structure by connecting, a transistor and a diode, to a power supply circuit including an illuminating circuit arranged at a distal part of an endoscope insertion portion.

SUMMARY OF THE INVENTION

Briefly, an optical adaptor for endoscope according to the present invention comprises, in an outer casing, a light emitter, serving as a light source for illumination, two terminals connected between the positive and negative electrodes of the light emitter to be externally projected from the inside of the outer casing, and static-electricity protecting means that is arranged between the positive and negative electrodes of the light emitter and prevents the static electricity from being applied to the light emitter.

Further, an endoscope apparatus according to the present invention comprises the optical adaptor for endoscope and an endoscope insertion portion comprising two terminals that electrically come into contact with the two terminals of the optical adaptor for endoscope, when being attached to the optical adaptor for endoscope.

The above and other objects, features and advantages of the invention will become more clearly understood from the following description referring to the accompanying drawings.

DETAILED DESCRIPTION OF THE PREFERRED EMBODIMENTS

Hereinbelow, a description is given of embodiments of the present invention with reference to the drawings.

First Embodiment

Figure 1:
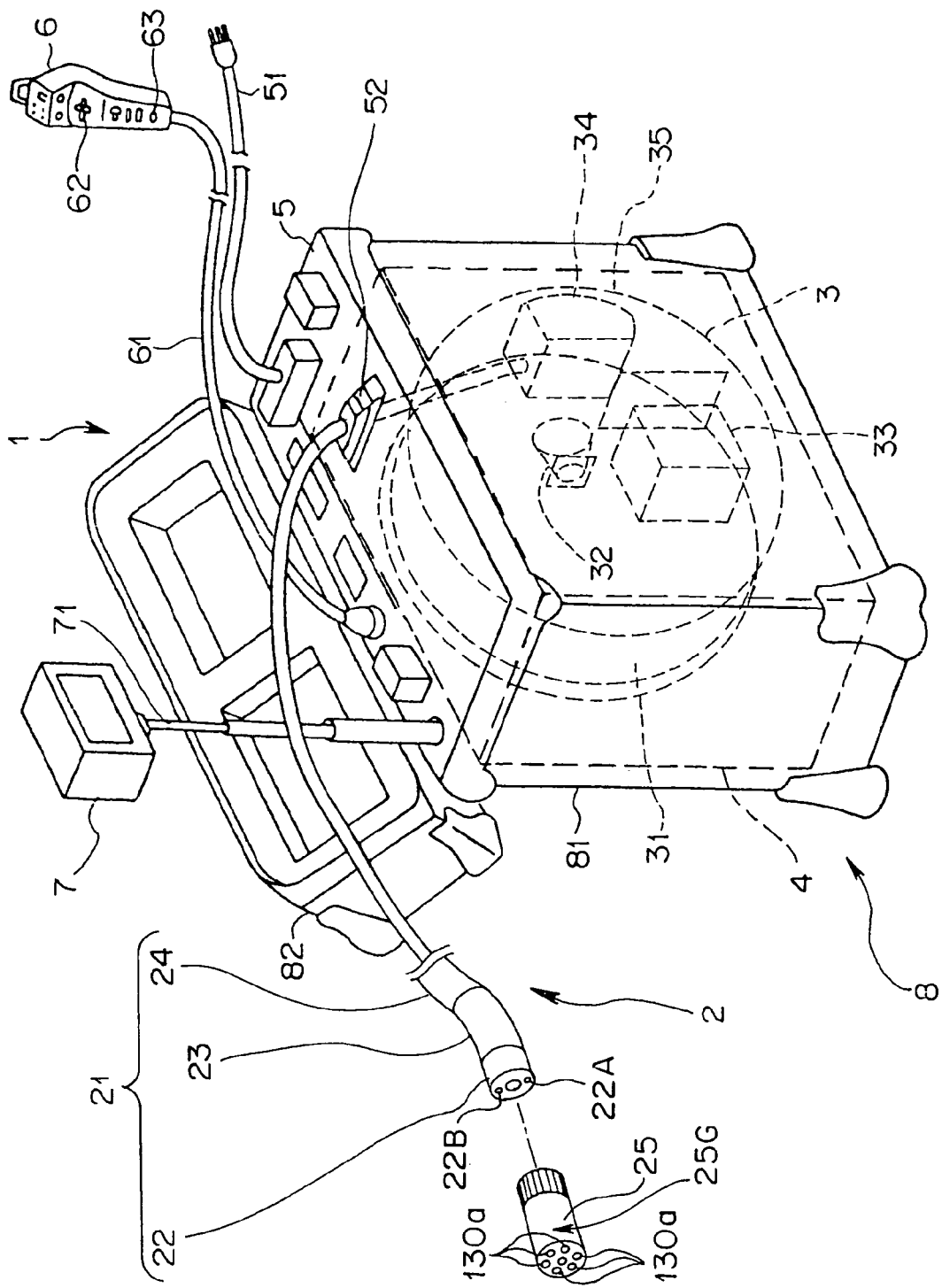
FIG. 1 is a perspective view showing an optical adaptor and an endoscope apparatus to which the optical adaptor is attached according to a first embodiment of the present invention.

FIG. 1 is a perspective view showing an optical adaptor and an endoscope apparatus to which the optical adaptor is attached according to a first embodiment of the present invention. According to the first embodiment, an industrial endoscope apparatus will be described as an endoscope apparatus.

Referring to FIG. 1, an endoscope apparatus 1 comprises a main portion comprising an industrial endoscope (hereinafter, referred to as an endoscope) 2 and an accommodating case 8. The accommodating case 8 comprises a box 81 and a cover 82 closably connected to the top of the box 81, and accommodates therein the endoscope 2 which is not used.

The box 81 of the accommodating case 8 comprises a drum unit 3, a light source unit 32, a camera control unit 33, an electrically bending driving unit 34, an electrically bending circuit unit 35, and a frame unit 4 which accommodates therein a power supply unit and the like.

The frame unit 4 rotatably supports the drum unit 3. The drum unit 3 comprises a tube member and is flange-shaped. Further, the drum unit 3 is an accommodating unit which winds an insertion unit 21 to an outer-circumferential portion 31 upon accommodating therein the endoscope 2.

A front panel 5 having switches, connectors, and a duct for feeding/discharging the air is formed to the top of the box 81. Specifically, one end of an AC cable 51 for supplying the power to the endoscope 2 and the members accommodated in the frame unit 4 is connected to the top surface of the front panel 5.

An expandable pole 71 for rotatably supporting a monitor 7 for displaying an image of an inspection part picked-up by the endoscope 2 is connected to the top surface of the front panel 5. Further, a cable 61 of a remote controller 6 is detachably connected to the top surface of the front panel 5.

The remote controller 6 has a joy stick 62 which is a bending input control unit upon bending a bending portion 23 of the insertion unit 21 in the endoscope 2. The remote controller 6 comprises an on-power button 63 for endoscope 2 and members accommodated in the frame unit 4.

Further, a rubber member 52 for preventing the bending is arranged, having an opening for putting in/out the insertion unit 21 of the endoscope 2 to the box 81. The rubber member 52 for preventing the bending prevents the bending of the insertion unit 21 in the endoscope 2 near the exit of the front panel 5 upon taking out the insertion unit 21 in the endoscope 2 from the box 81.

The endoscope 2 has the soft and elongated insertion unit 21. Upon using the endoscope 2, the insertion unit 21 is extended via the rubber member 52 for preventing the bending from the front panel 5. The insertion unit 21 has, in order from the distal end, a rigid distal-part main body 22, a bending portion 23, and an elongated and flexible portion 24.

The bending portion 23 is bendable in the multi-directions. Further, the bending portion 23 is bent by operating the remote controller 6, thereby changing, in the desired direction, the observing direction of an objective (not shown) of an observation optical system (not shown) arranged in the distal part main body 22.

Terminals 22A and 22B for electrically connecting a contact ends of a terminal 130A on the anode side and a terminal 130B on the cathode side of the LEDs 130 (refer to FIG. 2) arranged in the optical adaptor 25 are arranged, upon attaching an optical adaptor for endoscope (hereinafter, referred to as an optical adaptor) 25, which will be described later, to the distal end of the distal-part main body 22.

When the optical adaptor 25 is attached to the distal end of the distal-part main body 22, the terminals 22A and 22B supply the power from the power supply arranged to the frame unit 4 to the terminal 130A on the anode side and the terminal 130B on the cathode side of the optical adaptor 25.

The optical adaptor 25 for converting the optical property such as a field-of-view direction and a field-of-view angle is detachably attached to the distal end of the distal-part main body 22 in the endoscope insertion portion 21. The optical adaptor 25 has a cylindrical outer casing 25G containing metal, and the LEDs 130 comprising LEDs 130d1 to 130d4, serving as a plurality of light emitters, are arranged at the distal part in the outer casing 25G.

The LEDs 130 are arranged in the distal part of the optical adaptor 25, thereby improving the illuminating capacity of the endoscope 2. The arranging positions of the LEDs 130d are changed, thereby changing the illuminating direction to the inspection part.

Figure 2:
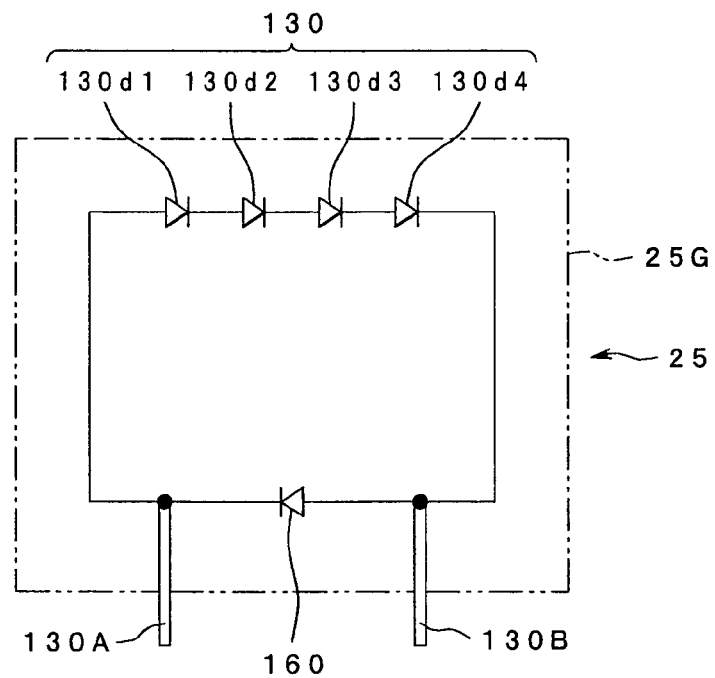
FIG. 2 is an electrical circuit diagram showing a light-emission circuit of LEDs arranged in an outer casing of the optical adaptor shown in FIG. 1.

FIG. 2 is an electrical circuit diagram showing a light-emission circuit of LEDs 130 arranged in the outer casing 25G of the optical adaptor 25 shown in FIG. 1.

Referring to FIG. 2, the LEDs 130 are structured by serially connecting the four LEDs 130d1 to 130d4 in the outer casing 25G of the optical adaptor 25. The terminal 130A on the anode side and the terminal 130B on the cathode side serving as terminals are connected between the anode of the LED 130d1 and the cathode of the LED 130d4 forming the LEDs 130, serving as the positive and negative electrodes of the LEDs 130. Hereinbelow, the anode of the LED 130d1 is referred to as the anode of the LEDs 130, and the cathode of the LED 130d4 is referred to as the cathode of the LEDs 130.

Specifically, the terminal 130A on the anode side and the terminal 130B on the cathode side are connected between the anode and the cathode of the LEDs 130 so that the contact ends of the terminal 22A of the terminal 130A on the anode side and the terminal 22B of the terminal 130B on the cathode side are projected to the insertion unit 21 from the outer casing 25G.

A diode 160, serving as static-electricity protecting means, is connected between the anode and the cathode of the LEDs 130. The anode of the diode 160 is connected to the cathode of the LEDs 130, and the cathode of the diode 160 is connected to the anode of the LEDs 130.

Next, the operation of the optical adaptor 25 with the above-mentioned structure will be described.

When the optical adaptor 25 is attached to the distal-part main body 22 of the insertion unit 21, the contact ends of the terminal 130A on the anode side and the terminal 130B on the cathode side electrically come into contact with the terminals 22A and 22B arranged to the distal-part main body 22.

Thus, the power supplied from the insertion unit 21 side is applied to the LEDs 130 via the terminal 130A on the anode side and the terminal 130B on the cathode side, thereby emitting the light from the LEDs 130.

If the static electricity is generated after detaching the optical adaptor 25 from the distal-part main body 22, the static electricity flows to the terminal 130A on the anode side and the terminal 130B on the cathode side.

Specifically, upon applying the positive electrostatic voltage to the terminal 130B on the cathode side between the terminal 130A on the anode side and the terminal 130B on the cathode side, since the diode 160 is connected between the anode and the cathode of the LEDs 130, the static electricity with a high voltage flows to the terminal 130A on the anode side via the diode 160.

Thus, even if the electrostatic voltage is applied to the terminal 130B on the cathode side by the operator, the electrostatic voltage is not applied between the anode and the cathode of the LEDs 130. Therefore, since the LEDs 130 are protected from the static electricity, the LEDs 130 are not easily broken by the static electricity.

Since the earth is not necessary for the operator upon operating the optical adaptor 25, the optical adaptor 25 is easily operated.

As mentioned above, the optical adaptor with high reliability against the applied static electricity is realized.

Figure 3:
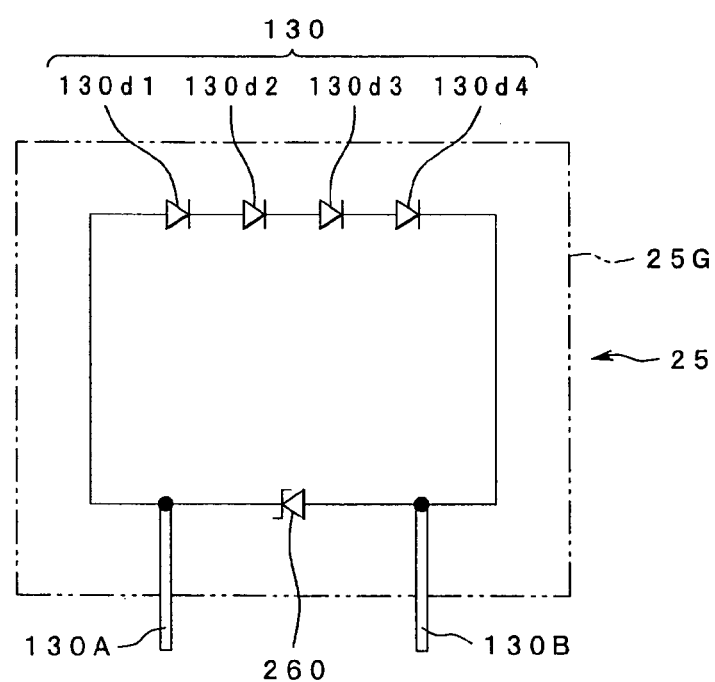
FIG. 3 is an electrical circuit diagram showing a light-emission circuit of LEDs arranged in the outer casing of the optical adaptor shown in FIG. 1 according to a modification.

Hereinbelow, a modification of the first embodiment will be described with reference to FIG. 3. FIG. 3 is an electrical circuit diagram showing a light-emission circuit of LEDs 130 arranged in the outer casing 25G of the optical adaptor 25 shown in FIG. 1 according to the modification.

According to the first embodiment, the diode 160, serving as static-electricity protecting means, is connected between the anode and the cathode of the LEDs 130. The present invention is not limited to this and a zener diode 260, serving as static-electricity protecting means, may be connected between the anode and the cathode of the LEDs 130. The anode of the zener diode 260 is connected to the cathode of the LEDs 130, and the cathode of the zener diode 260 is connected to the anode of the LEDs 130.

Next, the operation of the optical adaptor 25 with the above structure will be described.

Even if the static electricity is generated after detaching the optical adaptor 25 from the distal-part main body 22, the static electricity flows to the terminal 130A on the anode side and the terminal 130B on the cathode side.

Specifically, upon applying the positive electrostatic voltage to the terminal 130A on the anode side between the terminal 130A on the anode side and the terminal 130B on the cathode side, since the zener diode 260 is connected between the anode and the cathode of the LEDs 130, the static electricity with a high voltage flows to the terminal 130B on the cathode side via the zener diode 260.

Thus, even if the electrostatic voltage is applied to the terminal 130A on the anode side by the operator, the electrostatic voltage is not applied between the anode and the cathode of the LEDs 130. Therefore, since the LEDs 130 are protected from the static electricity, the LEDs 130 are not easily broken by the static electricity.

Since the earth is not necessary for the operator upon operating the optical adaptor 25, the optical adaptor 25 is easily operated.

As mentioned above, the optical adaptor with high reliability against the applied static electricity is realized.

Figure 4:
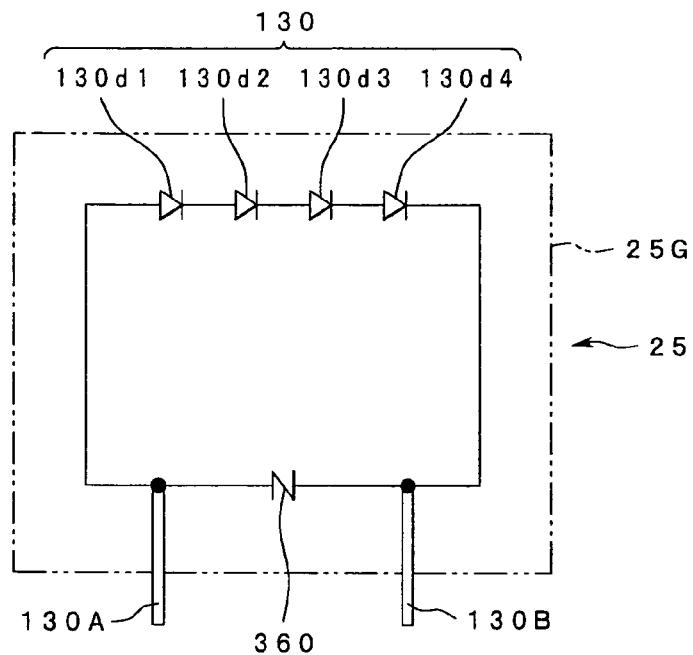
FIG. 4 is an electrical circuit diagram showing another light-emission circuit of LEDs arranged in the outer casing of the optical adaptor shown in FIG. 1 according to another modification.

Hereinbelow, another modification of the first embodiment will be described with reference to FIG. 4. FIG. 4 is an electrical circuit diagram showing a light-emission circuit of LEDs 130 arranged in the outer casing 25G of the optical adaptor 25 shown in FIG. 1 according to the other modification.

According to the first embodiment, the diode 160 or zener diode 260, serving as static-electricity protecting means, is connected between the anode and the cathode of the LEDs 130. However, the present invention is not limited to this and a varistor 360, serving as static-electricity protecting means, may be connected between the anode and the cathode of the LEDs 130 as shown in FIG. 4.

The varistor 360 does not have the directivity when the current flows but has characteristic of turning to the on-state at a predetermined voltage or more. Therefore, it is possible to obtain the same advantage as that of connecting the diode 160 or zener diode 260, serving as static-electricity protecting means, between the anode and the cathode of the LEDs 130.

Second Embodiment

Figure 5:
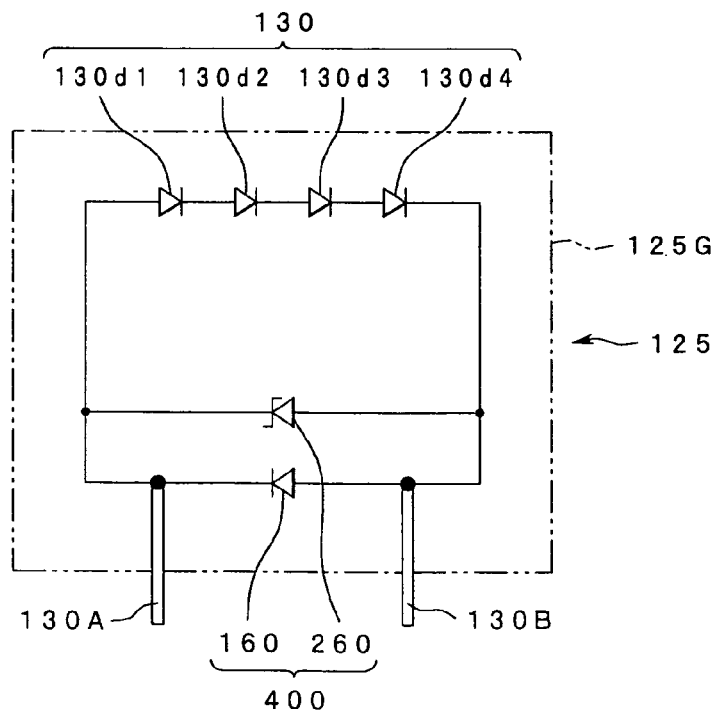
FIG. 5 is an electrical circuit diagram showing a light-emission circuit of LEDs arranged in an outer casing of an optical adaptor in an endoscope apparatus according to a second embodiment of the present invention.

FIG. 5 is an electrical circuit diagram showing a light-emission circuit of LEDs arranged in an outer casing of an optical adaptor in an endoscope apparatus according to a second embodiment of the present invention.

The structure of the light-emission circuit of the optical adaptor according to the second embodiment is different from the light-emission circuit of the optical adaptor shown in FIGS. 1 to 4, in that the static-electricity protecting means connected between the anode and the cathode of the LEDs 130 comprises a parallel circuit. Only the different point is described, the same reference numeral denotes the same component as that according to the first embodiment, and a description thereof is omitted.

Referring to FIG. 5, the LEDs 130 are structured by serially connecting, for example, the four LEDs 130$d1$ to 130$d4$ in an outer casing 125G of an optical adaptor 125. The terminal 130A on the anode side and the terminal 130B on the cathode side serving as terminals are connected between the anode and the cathode of the LEDs 130.

Specifically, the terminal 130A on the anode side and the terminal 130B on the cathode side are connected between the anode and the cathode of the LEDs 130 so that the contact ends of the terminals 22A and 22B of the terminal 130A on the anode side and the terminal 130B on the cathode side are projected to the insertion unit 21 side from the outer casing 125G.

A parallel circuit 400 of the diode 160 and the zener diode 260, serving as static-electricity protecting means, is connected between the anode and the cathode of the LEDs 130. The anodes of the diode 160 and the zener diode 260 are connected to the cathode of the LEDs 130, and the cathodes of the diode 160 and the zener diode 260 are connected to the anode of the LEDs 130.

Next, the operation of the optical adaptor 125 with the above-mentioned structure will be described.

When the optical adaptor 125 is attached to the distal-part main body 22 of the insertion unit 21, the contact ends of the terminal 130A on the anode side and the terminal 130B on the cathode side electrically come into contact with the terminals 22A and 22B arranged to the distal part main body 22.

Thus, the power supplied from the insertion unit 21 is applied to the LEDs 130 via the terminal 130A on the anode side and the terminal 130B on the cathode side, thereby emitting the light from the LEDs 130.

Even if the static electricity is generated after detaching the optical adaptor 125 from the distal-part main body 22, the static electricity flows to the terminal 130A on the anode side and the terminal 130B on the cathode side.

Specifically, upon applying the positive electrostatic voltage to the terminal 130B on the cathode side between the terminal 130A on the anode side and the terminal 130B on the cathode side, since the diode 160 is connected between the anode and the cathode of the LEDs 130, the static electricity with a high voltage flows to the terminal 130A on the anode side via the diode 160.

Further, upon applying the positive electrostatic voltage to the terminal 130A on the anode side between the terminal 130A on the anode side and the terminal 130B on the cathode side, since the zener diode 260 is connected between the anode and the cathode of the LEDs 130, the static electricity with a high voltage flows to the terminal 130B on the cathode side via the zener diode 260.

Thus, even if the electrostatic voltage is applied to the terminal 130A on the anode side or the terminal 130B on the cathode side, the electrostatic voltage is not applied between the anode and the cathode of the LEDs 130. Therefore, since the LEDs 130 are protected from the static electricity, the LEDs 130 are not easily broken by the static electricity.

Since the earth is not necessary for the operator upon operating the optical adaptor 125, the optical adaptor 125 is easily operated.

As mentioned above, the optical adaptor with high reliability against the applied static electricity is realized.

Figure 6:
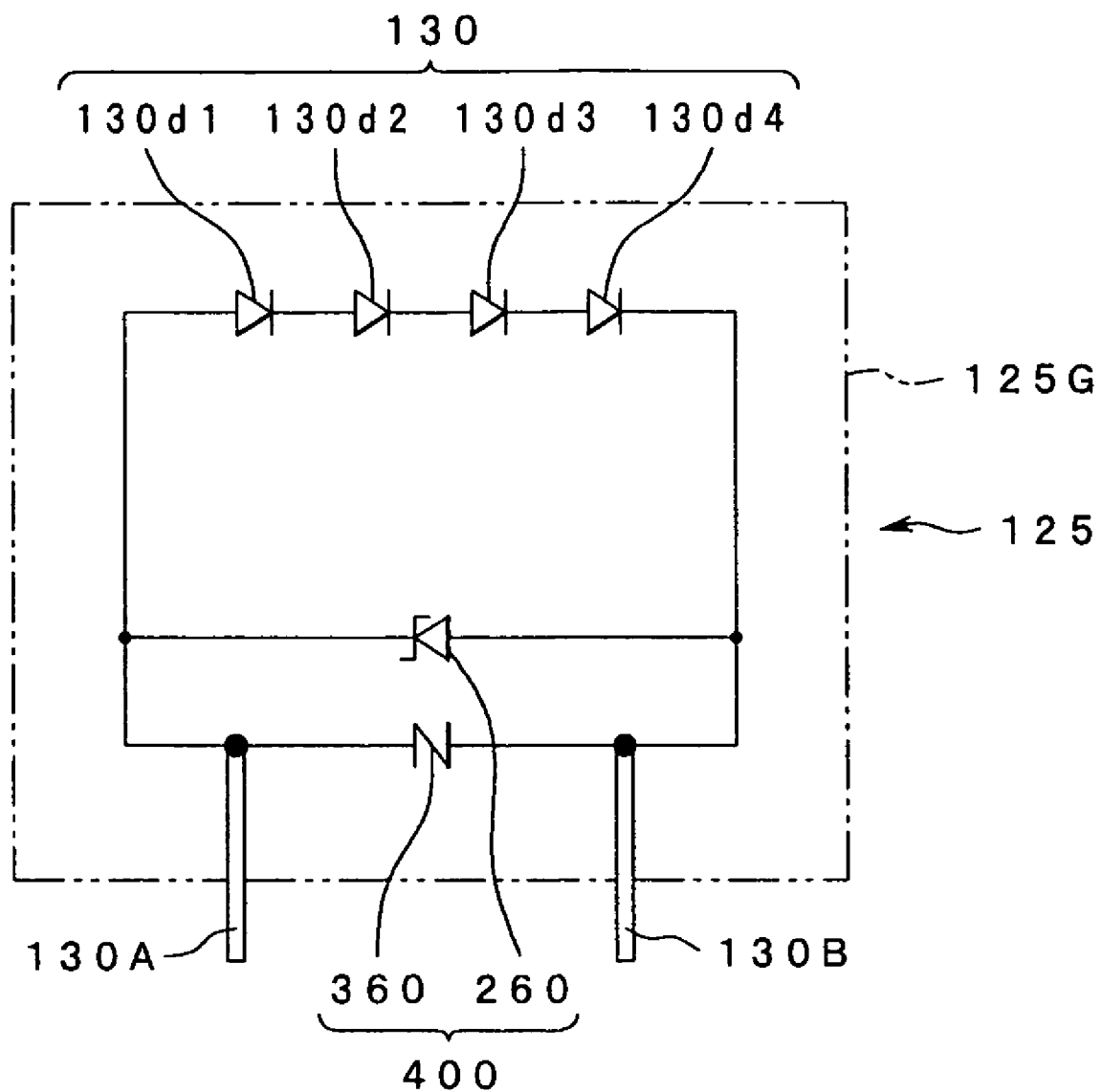
FIG. 6 is an electrical circuit diagram showing a light-emission circuit of LEDs arranged in the outer casing of the optical adaptor shown in FIG. 5 according to another modification.

Hereinbelow, a modification of the second embodiment will be described with reference to FIG. 6. FIG. 6 is an electrical circuit diagram showing a light-emission circuit of LEDs 130 arranged in the outer casing 125G of the optical adaptor 125 shown in FIG. 5 according to the modification.

According to the second embodiment, the parallel circuit 400 of the diode 160 and the zener diode 260, serving as static-electricity protecting means, is connected between the anode and the cathode of the LEDs 130.

However, the present invention is not limited to this and the parallel circuit 400 of the varistor 360 and the zener diode 260, serving as static-electricity protecting means, may be connected between the anode and the cathode of the LEDs 130, thus the same advantage as that of the present embodiment can be obtained.

Although not shown, it is possible to obtain the same advantage as that of the present embodiment by connecting the parallel circuit 400 of the varistor 360 and the diode 160, serving as static-electricity protecting means, between the anode and the cathode of the LEDs 130.

Third Embodiment

Figure 7:
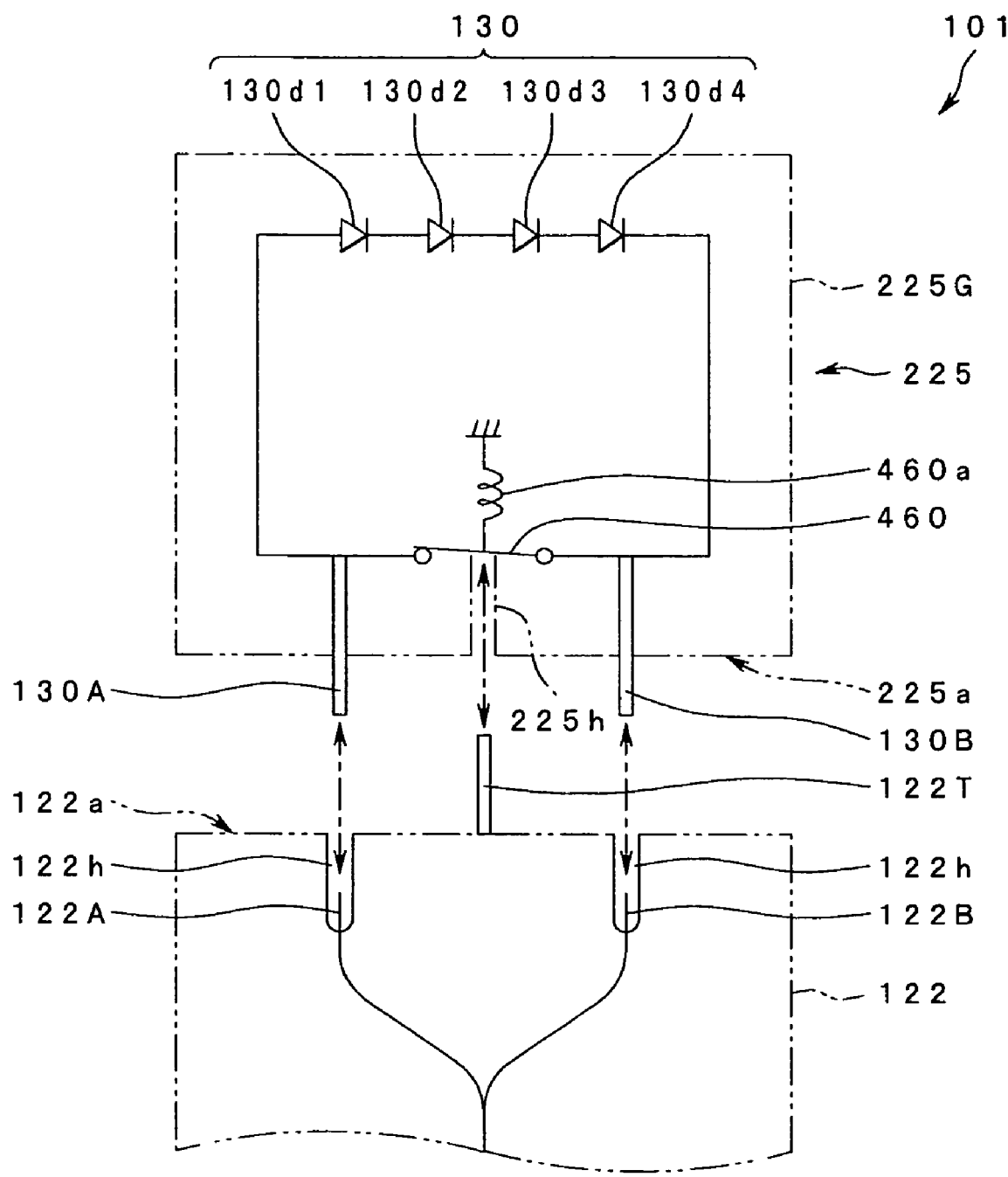
FIG. 7 is a connection structure diagram showing the connection between an optical adaptor in an endoscope apparatus and a distal-part main body according to a third embodiment of the present invention.

FIG. 7 is a connection structure diagram showing the connection between an optical adaptor in an endoscope apparatus and a distal-part main body according to a third embodiment of the present invention.

The structure of the endoscope apparatus according to the third embodiment is different from the endoscope apparatus shown in FIGS. 1 to 6 according to the first embodiment and the second embodiment, in that countermeasures against the static electricity for LEDs 130 arranged in the outer casing of the optical adaptor is performed not only with the light emission circuit arranged in the optical adaptor, but also with distal-part main body of the endoscope inserting unit to which the optical adaptor is connected. Only the different point is described, the same reference numeral denotes the same component as that according to the first and second embodiments, and a description thereof is omitted.

Referring to FIG. 7, terminals 122A and 122B which electrically come into contact with the contact terminals of the terminal 130A on the anode side and the terminal 130B on the cathode side of the LEDs 130 arranged in an optical adaptor 225 are arranged upon attaching the optical adaptor 225, which will be described later, to the distal end of a distal-part main body 122 of the endoscope 2 in an endoscope apparatus 101.

Specifically, two holes 122h are pierced through a distal surface 122a of the distal-part main body 122. The terminals 122A and 122B are arranged to the holes 122h. When the optical adaptor 225 is attached to the distal end of the distal-part main body 122, the terminals 122A and 122B come into contact with the contact ends of the terminal 130A on the anode side and the terminal 130B on the cathode side of the optical adaptor 225, thereby supplying the power form the power supply arranged to the frame unit 4 to the terminal 130A on the anode side and the terminal 130B on the cathode side.

A projected pin 122T, serving as a projected portion for opening a normally-closed switch 460 arranged in the optical adaptor 225 upon attaching the optical adaptor 225, which will be described later, is arranged substantially in the center of the distal surface 122a.

The projected length of the projected pin 122T is longer than the contact length when the contact ends of the terminal 130A on the anode side and the terminal 130B on the cathode side of the optical adaptor 225 come into contact with the terminals 122A and 122B of the distal-part main body 122 upon attaching the optical adaptor 225 to the distal part main body 122.

The optical adaptor 225 for converting the optical property such as the field-of-view direction and the field-of-view angle is detachably attached to the distal end of the distal-part main body 122 in the insertion unit 21. The optical adaptor 225 has a cylindrical outer casing 225G containing metal, and the LEDs 130 comprising LEDs 130d1 to 130d4, serving as a plurality of light emitters, are arranged at the distal part in the outer casing 225G.

The LEDs 130 are arranged in the distal part of the optical adaptor 225, thereby improving the illuminating capacity of the endoscope 2. The arranging positions of the LEDs 130d are changed, thereby changing the illuminating direction to the inspection part.

Specifically, the LEDs 130 are structured by serially connecting the four LEDs 130d1 to 130d4 in the outer casing 225G of the optical adaptor 225. The terminal 130A on the anode side and the terminal 130B on the cathode side, serving as terminals, are connected between the anode of the LED 130d1 and the cathode of the LED 130d4 forming the LEDs 130, serving as the anode and the cathode of the LEDs 130.

More specifically, the terminal 130A on the anode side and the terminal 130B on the cathode side are connected between the anode and the cathode of the LEDs 130 so that the contact ends of the terminals 122A and 122B of the terminal 130A on the anode side and the terminal 130B on the cathode side are projected to the insertion unit 21 side from the outer casing 225G.

The normally-closed switch 460, serving as static-electricity protecting means, comprising, for example, an energizing spring 460a is connected between the anode and the cathode of the LEDs 130. The anode and the cathode of the LEDs 130 is short-circuited by the normally-closed switch 460 when the optical adaptor 225 is not attached to the distal-part main body 122. The normally-closed switch 460 may be a known normally-closed switch without using the energizing spring 460a.

A hole 225h that pierces through the position of the normally-closed switch 460 arranged in the optical adaptor 225 is formed at the facing position of the projected pin 122T on a surface 225a of the optical adaptor 225 which comes into contact with the distal surface 122a of the distal-part main body 122 upon attaching the optical adaptor 225 to the distal-part main body 122.

Next, a description is given of the operation of the optical adaptor 225 in the endoscope apparatus 101 with the above-mentioned structure.

When the optical adaptor 225 is not attached to the distal-part main body 122, the normally-closed switch 460 always connects between the anode and the cathode of the LEDs 130. Therefore, when the optical adaptor 225 is not attached to the distal-part main body 122, the anode and the cathode of the LEDs 130 are always short-circuited.

Thus, if the electrostatic voltage is applied to the terminal 130A on the anode side or the terminal 130B on the cathode side, the electrostatic voltage is not applied to between the anode and the cathode of the LEDs 130. Since the LEDs 130 are protected from the static electricity, the LEDs 130 are not easily electrically broken.

When the optical adaptor 225 is attached to the distal-part main body 122, the projected pin 122T arranged to the distal surface 122a of the distal-part main body 122 is fit into the hole 225h formed onto the surface 225a of the optical adaptor 225.

The projected pin 122T presses the normally-closed switch 460, thereby opening the normally-closed switch 460. Thus, between the anode and the cathode of the LEDs 130 are conductive.

After that, the terminal 130A on the anode side and the terminal 130B on the cathode side of the optical adaptor 225 are fit into the two holes 122h formed to the distal-part main body 122 respectively and the contact ends come into contact with the terminals 122A and 122B. Thus, the terminals 122A and the terminal 122B of the distal-part main body 122 supply the power from the power supply to the terminal 130A on the anode side and the terminal 130B on the cathode side. Then, the LEDs 130 emit the light.

Therefore, when the optical adaptor 225 is attached to the distal end of the distal-part main body 122, between the anode and the cathode of the LEDs 130 are short-circuited just before the terminals 122A and 122B of the distal-part main body 122 come into contact with the contact ends of the terminal 130A on the anode side and the terminal 130B on the cathode side of the optical adaptor 225. After entering the conductive state, the terminals 122A and 122B of the distal-part main body 122 promptly come into contact with the contact ends of the terminal 130A on the anode side and the terminal 130B on the cathode side of the optical adaptor 225, thereby supplying the power.

The projected length of the projected pin 122T is longer than the contact length when the contact ends of the terminal 130A on the anode side and the terminal 130B on the cathode side of the optical adaptor 225 come into contact with the terminals 122A and 122B of the distal-part main body 122 upon attaching the optical adaptor 225 to the distal-part main body 122. Therefore, when between the anode and the cathode of the LEDs 130 are short-circuited, the electrostatic voltage is not applied to the LEDs 130.

If the electrostatic voltage is applied to the terminal 130A on the anode side or the terminal 130B on the cathode side upon attaching the optical adaptor 225 to the distal-part main body 122, the electrostatic voltage is not applied between the anode and the cathode of the LEDs 130 by the operator. Therefore, since the LEDs 130 are protected from the static electricity, the LEDs 130 are not easily broken by the static electricity.

Since the earth is not necessary for the operator upon operating the optical adaptor 225, the optical adaptor 225 is easily operated.

As mentioned above, an endoscope with the optical adaptor with high reliability against the applied static electricity is realized.

Fourth Embodiment

Figure 8:
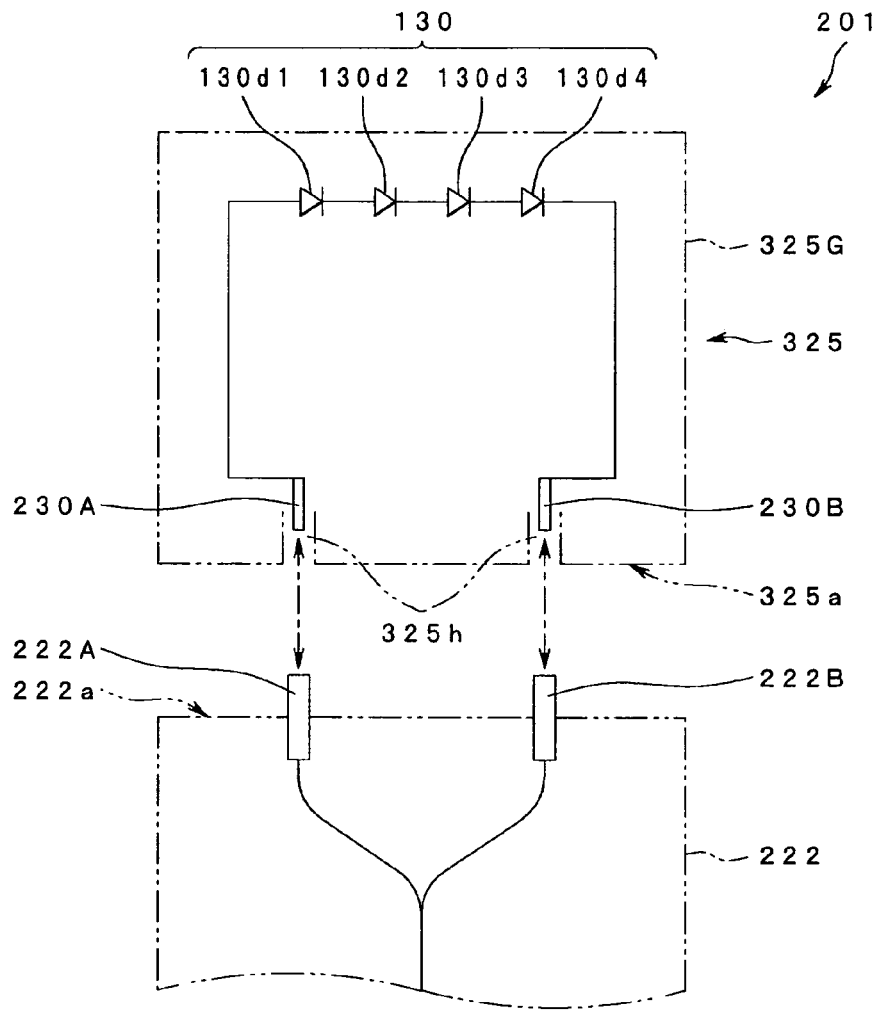
FIG. 8 is a connection structure diagram showing the connection between an optical adaptor in an endoscope apparatus and a distal-part main body according to a fourth embodiment of the present invention.
Figure 9:
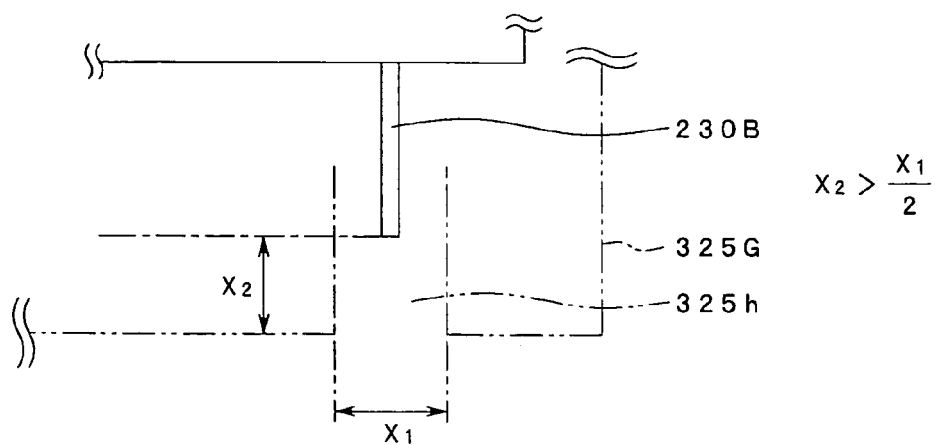
FIG. 9 is a diagram showing the arrangement position in the optical adaptor of a terminal on the anode or of a terminal of the cathode shown in FIG. 8.

FIG. 8 is a connection structure diagram showing the connection between an optical adaptor in an endoscope apparatus and a distal-part main body according to a fourth embodiment of the present invention. FIG. 9 is a diagram showing the arrangement position in the optical adaptor of the terminal 130A on the anode or of the terminal 130B on the cathode shown in FIG. 8.

The structure of the endoscope apparatus according to the fourth embodiment is different from the endoscope apparatus shown in FIG. 7 according to the third embodiment in that the problem of the static electricity is solved without any switches. Only different points are described, the same reference numeral denotes the same component as that according to the third embodiment, and a description thereof is omitted.

Referring to FIG. 8, when an optical adaptor 325, which will be described later, is attached to the distal end of a distal-part main body 222 of the endoscope 2 in an endoscope apparatus 201, terminals 222A and 222B which electrically come into contact with contact ends of a terminal 230A on the anode side and a terminal 230B on the cathode side of the LEDs 130 in the optical adaptor 325, are projected from a distal surface 222a of the distal-part main body 222.

When the optical adaptor 325 is attached to the distal-part main body 222, the terminals 222A and 222B come into contact with the contact ends of the terminal 230A on the anode side and the terminal 230B on the cathode side of the optical adaptor 325, thereby supplying the power from a power supply to the terminal 230A on the anode side and the terminal 230B on the cathode side.

The optical adaptor 325 for converting the optical property such as the field-of-view direction and the field-of-view angle is detachably attached to the distal end of the distal part main body 222 in the insertion unit 21. The optical adaptor 325 has a cylindrical outer casing 325G containing metal, and the LEDs 130 comprising LEDs 130d1 to 130d4, serving as a plurality of light emitters, are arranged at the distal part in the outer casing 325G.

The LEDs 130 are arranged in the distal part of the optical adaptor 325, thereby improving the illuminating capacity of the endoscope 2. The arranging positions of the LEDs 130d are changed, thereby changing the illuminating direction to the inspection part.

Specifically, the LEDs 130 are structured by serially connecting the four LEDs 130d in the outer casing 325G of the optical adaptor 325. The terminal 230A on the anode side and the terminal 230B on the cathode side, serving as terminals, are connected between the anode and the cathode of the LEDs 130, serving as the anode and the cathode of the LEDs 130.

More specifically, the terminal 230A on the anode side and the terminal 230B on the cathode side are connected between both the anode and the cathode of the LEDs 130 so that the contact ends of the terminals 222A and 222B of the terminal 230A on the anode side and the terminal 230B on the cathode side are caved in the outer casing 325G from a surface 325a on the insertion unit side of the optical adaptor 325.

A hole 325h that pierces through the terminal 230A on the anode side and the terminal 230B on the cathode side arranged in the outer casing 325G of the optical adaptor 325 is formed at the facing position of the terminals 222A and 222B on a surface 325a of the optical adaptor 325.

Referring to FIG. 9, reference symbol X1 denotes the diameter of the hole 325h, reference symbol X2 denotes the depth from the surface 325a of the optical adaptor 325 to the contact ends of the terminal 230A on the anode side and the terminal 230B on the cathode side, and a relation of $[(X1 \cdot \frac{1}{2}) < X2]$ is established.

Next, a description is given of the operation of the optical adaptor 325 in the endoscope apparatus 201 with the above-mentioned structure.

When an optical adaptor 325 is attached to the distal-part main body 222, terminals 222A and 222B of the distal-part main body 222 come into contact with the terminal 230A on the anode side and the terminal 230B on the cathode side. After that, the LEDs 130 emit light.

Even if the static electricity is generated at the terminals 222A and 222B of the distal-part main body 222 in this case, since the contact ends of the terminal 230A on the anode side and the terminal 230B on the cathode side caved from the surface 325a of the optical adaptor 325 by the depth X2 satisfying the relation of $[(X1 \cdot \frac{1}{2}) < X2]$, the static electricity is transmitted to an outer member of the optical adaptor 325 before the terminals 222A and 222B come into contact with the contact ends of the terminal 230A on the anode side and the terminal 230B on the cathode side.

Even if the electrostatic voltage is applied to the terminal 222A or the terminal 222B upon attaching the optical adaptor 325 to the distal-part main body 222, the electrostatic voltage is not applied between the anode and the cathode of the LEDs 130 by the operation. Therefore, since the LEDs 130 are protected from the static electricity, the LEDs 130 are not easily broken by the static electricity.

Further, when the optical adaptor 325 is not attached to the distal-part main body 222, since the contact ends of the terminal 230A on the anode side and the terminal 230B on the cathode side caved from the surface 325a of the optical adaptor 325 by the depth X2 satisfying the relation of [(X1·½) <X2], the static electricity around the contact ends of the terminal 230A on the anode side and the terminal 230B on the cathode side is transmitted to the outer member of the optical adaptor 325.

Therefore, when the optical adaptor 325 is not attached to the distal-part main body 222, the LEDs 130 are protected from the static electricity. Thus, the LEDs 130 are not easily broken by the static electricity.

Since the earth is not necessary for the operator upon operating the optical adaptor 325, the optical adaptor 325 is easily operated.

As mentioned above, the optical adaptor with high reliability is realized against the applied static electricity.

Fifth Embodiment

Figure 10:
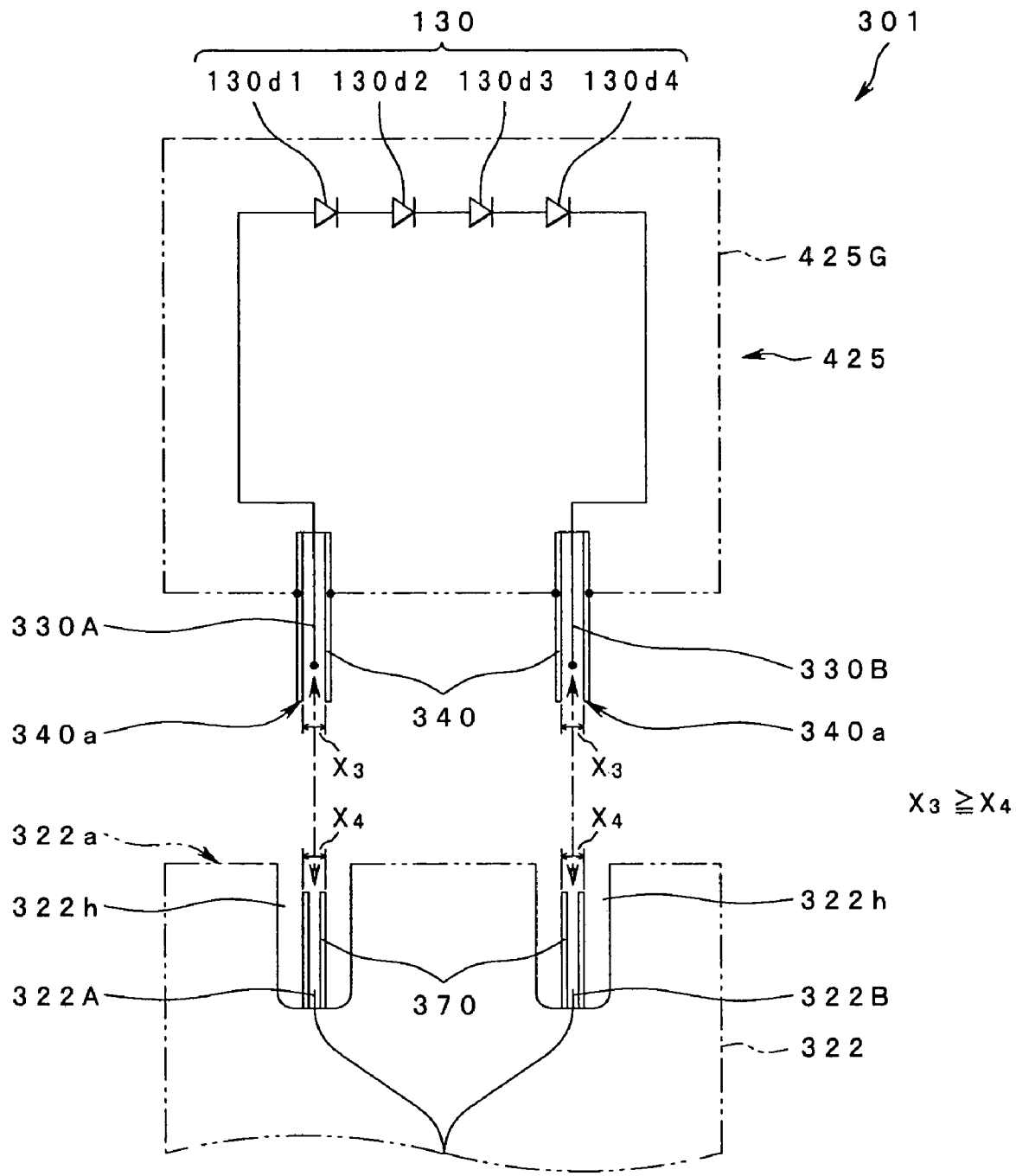
FIG. 10 is a connection structure diagram showing the connection between an optical adaptor in an endoscope apparatus and a distal-part main body according to a fifth embodiment of the present invention.

FIG. 10 is a connection structure diagram showing the connection between an optical adaptor in an endoscope apparatus and a distal-part main body according to a fifth embodiment of the present invention.

The structure of the endoscope apparatus according to the fifth embodiment is different from the endoscope apparatus shown in FIGS. 8 and 9 according to the fourth embodiment in that the terminal on the anode side and the terminal on the cathode are arranged in a protecting member arranged to the optical adaptor. Only different points are described, the same reference numeral denotes the same component as that according to the fourth embodiment, and a description thereof is omitted.

Referring to FIG. 10, when an optical adaptor 425 is attached to the distal end of a distal-part main body 322 of the endoscope 2 in an endoscope apparatus 301, terminals 322A and 322B have the coaxial structure of a terminal 330A on the anode side and a terminal 330B on the cathode side, which electrically come into contact with contact ends of the terminal 330A on the anode side and the terminal 330B on the cathode side of the LEDs 130 in the optical adaptor 425.

Specifically, two holes 322h are pierced through a distal surface 322a of the distal-part main body 322. For example, circular cylinders (hereinafter, referred to as cylinders) 370 are arranged to the two holes 322h with an outer diameter X4. Further, the terminals 322A and 322B are arranged in the space of the cylinder 370.

When the optical adaptor 425 is attached to the distal-part main body 322, the terminals 322A and 322B come into contact with the contact ends of the terminal 330A on the anode side and the terminal 330B on the cathode side of the optical adaptor 425, thereby supplying the power from a power supply to the terminal 330A on the anode side and the terminal 330B on the cathode side. The power is supplied from the power supply arranged to the frame unit 4 to the terminal 330A on the anode side and the terminal 330B on the cathode side.

The optical adaptor 425 for converting the optical property such as the field-of-view direction and the field-of-view angle is detachable to the distal end of the distal-part main body 322 in the insertion unit 21. The optical adaptor 425 has a cylindrical outer casing 425G containing metal.

A cylinder 340, serving as a protecting member containing metal, for example, has an inner diameter X3 that is equal to the outer diameter X4 of the cylinder 370 or more and provided at the facing positions of the holes 322h formed to the distal-part main body 322 of the optical adaptor 425. The cylinder 340 is shielded by the outer casing 425G of the optical adaptor 425 so as to communicate with the inside and the outside of the outer casing 425G, and is projected to the insertion unit 21 from the inside of the outer casing 425G of the optical adaptor 425. In this case, the outer casing 425G of the optical adaptor 425 and the cylinder 340 have the same potential.

When the optical adaptor 425 is attached to the distal-part main body 322, the cylinder 370 arranged to the holes 322h of the distal part main body 322 is inserted in the cylinder 340.

The LEDs 130 comprising the LEDs 130d are arranged at the distal part in the outer casing 425G of the optical adaptor 425. The arrangement of the LEDs 130 at the distal end of the optical adaptor 425 enables the improvement in illuminating capacity of the endoscope 2. The arrangement positions of the LEDs 130d are changed, thereby changing the illuminating direction to the inspection part.

Specifically, the LEDs 130 are structured by serially connecting the four LEDs 130d in the outer casing 425G of the optical adaptor 425. The terminal 330A on the anode side and the terminal 330B on the cathode side, serving as terminals, in the cylinder 340 are connected between the anode and the cathode of the LED 130, serving as the anode and the cathode of the LEDs 130.

Further specifically, the contact ends of the terminals 322A and 322B of the terminal 330A on the anode side and the terminal 330B on the cathode side are caved in the cylinder 340 to the outer casing 425G, rather than a projected surface 340a, serving as the surface of the cylinder 340.

The contact ends of the terminal 322A of the terminal 330A on the anode side and the terminal 322B of the terminal 330B on the cathode side are inserted in the cylinder 370 when the optical adaptor 425 is attached to the distal-portion main body 322 and the cylinder 370 is inserted in the cylinder 340.

Next, a description is given of the operation of the optical adaptor 425 in the endoscope apparatus 301 with the above-mentioned structure.

When the optical adaptor 425 is attached to the distal-part main body 322, the cylinder 340 arranged to the optical adaptor 425 is fit into the hole 322h of the distal-end main body. Further, the cylinder 370 of the distal part main body 322 is inserted in the cylinder 340 arranged to the optical adaptor 425.

Thus, the contact ends of the terminal 330A on the anode side and the terminal 330B on the cathode side arranged in the cylinder 340 come into contact with the terminals 322A and 322B in the cylinder 370. The LEDs 130 emit light.

Even if the static electricity is generated at the terminals 322A and 322B of the distal-part main body 322 and in the cylinder 370, the static electricity is transmitted to the cylinder 340 before the terminals 322A and 322B come into contact with the contact ends of the terminal 330A on the anode side and the terminal 330B on the cathode side because the contact ends of the terminal 330A on the anode side and the terminal 330B on the cathode side are caved from the projected surface 340a of the cylinder 340.

Even if the electrostatic voltage is applied to the terminal 322A or 322B upon attaching the optical adaptor 425 to the distal-part main body 322, the electrostatic voltage is not applied between the anode and the cathode of the LEDs 130. Therefore, since the LEDs 130 are protected from the static electricity, the LEDs 130 are not easily broken by the static electricity.

Further, when the optical adaptor 425 is not attached to the distal-part main body 322, the contact ends of the terminal 330A on the anode side and the terminal 330B on the cathode side are caved from the projected surface 340a of the cylinder 340, the static electricity around the contact ends of the terminal 330A on the anode side and the terminal 330B on the cathode side is transmitted to the cylinder 340.

Therefore, since the LEDs 130 are protected from the static electricity even when the optical adaptor 425 is not attached to the distal-part main body 322, the LEDs 130 are not easily broken by the static electricity.

Since the earth is not necessary for the operator upon operating the optical adaptor 425, the optical adaptor 425 is easily operated.

As mentioned above, the optical adaptor with high reliability against the applied static electricity is realized.

According to the fifth embodiment, the cylinders 340 and 370, serving as protecting members, are cylindrical. However, the present invention is not limited to this and may be of any shape as long as the cylinder 340 can be fitted into the cylinder 370.

Further, according to the first to fifth embodiments, the LEDs 130 comprise the four LEDs 130d. However, the present invention is not limited to this and may comprise one or more.

Furthermore, according to the first to fifth embodiments, the LED is used as the light emitter. However, the present invention is not limited to this and may be any compact light-emitter used for light source of an endoscope.

Having described the preferred embodiments of the invention referring to the accompanying drawings, it should be understood that the present invention is not limited to those precise embodiments and various changes and modifications thereof could be made by one skilled in the art without departing form the spirit or scope of the invention as defined in the appended claims.

What is claimed is:

1. An optical adaptor for endoscope comprising, in an outer casing:
   at least one light emitter, having positive and negative electrodes, and serving as a light source for illumination;
   two terminals connected between the positive and negative electrodes of the light emitter to be externally projected from the inside of the outer casing; and
   a first and a second means for protecting the light emitter from static electricity, the first means for protecting being the outer casing to which static electricity escapes, and the second means for protecting being static-electricity protecting means that is arranged between the positive and negative electrodes of the light emitter and prevents the static electricity from being applied to the light emitter,
   wherein the outer casing contains metal, and
wherein the static-electricity protecting means is a parallel circuit comprising two of a diode, a zener diode, and a varistor.

2. An optical adaptor for endoscope comprising, in an outer casing:
   at least one light emitter, having positive and negative electrodes, and serving as a light source for illumination;
   two terminals connected between the positive and negative electrodes of the light emitter to be externally projected from the inside of the outer casing; and
   a first and a second means for protecting the light emitter from static electricity, the first means for protecting being the outer casing to which static electricity escapes, and the second means for protecting being static-electricity protecting means that is arranged between the positive and negative electrodes of the light emitter and prevents the static electricity from being applied to the light emitter,
   wherein the outer casing contains metal, and
wherein the static-electricity protecting means is a normally-closed switch.

3. An optical adaptor for endoscope according to claim 2, wherein the two terminals are caved in the outer casing from a surface of the outer casing.

4. An optical adaptor for endoscope according to claim 2, wherein the light emitter is a light-emission diode.

5. An optical adaptor for endoscope comprising, in an outer casing:
   at least one light emitter, having positive and negative electrodes, and serving as a light source for illumination;
   two terminals connected between the positive and negative electrodes of the light emitter to be externally projected from the inside of the outer casing; and
   a first and a second means for protecting the light emitter from static electricity, the first means for protecting being the outer casing to which static electricity escapes, and the second means for protecting being static-electricity protecting means that is arranged between the positive and negative electrodes of the light emitter and prevents the static electricity from being applied to the light emitter,
   wherein the outer casing contains metal, and
wherein a cylindrical protecting member communicated with the inside and the outside of the outer casing is connected to the outer casing to be externally projected from the inside of the outer casing, and
   the two terminals are caved in the protecting member from a surface of the projected protecting member,
   the cylindrical protecting member being a third means for protecting the light emitter from static electricity.

6. An optical adaptor for endoscope according to claim 5, wherein the protecting member contains metal.

7. An endoscope apparatus comprising:
   an optical adaptor for endoscope comprising, in an outer casing, the outer casing containing metal, at least one light emitter, having positive and negative electrodes, and serving as a light source for illumination, two terminals connected to the positive and negative electrodes of the light emitter to be externally projected from the inside of the outer casing, and a first and a second means for protecting the light emitter from static electricity, the first means for protecting being the outer casing to which static electricity escapes, and the second means for protecting being static-electricity protecting means that is arranged between the positive and negative electrodes of the light emitter and prevents the static electricity from being applied to the light emitter; and
   an endoscope insertion portion comprising two terminals that electrically come into contact with the two terminals of the optical adaptor for endoscope, when being attached to the optical adaptor for endoscope, and
wherein the static-electricity protecting means of the optical adaptor for endoscope is a normally-closed switch.

8. An endoscope apparatus according to claim 7, wherein the two terminals are caved in the outer casing from a surface of the outer casing.

9. An endoscope apparatus according to claim 8, wherein the endoscope insertion portion comprises two terminals that electrically come into contact with the two terminals in the outer casing, caved in the outer casing, when being attached to the optical adaptor for endoscope.

10. An endoscope apparatus comprising:
- an optical adaptor for endoscope comprising, in an outer casing, the outer casing containing metal, at least one light emitter, having positive and negative electrodes, and serving as a light source for illumination, two terminals connected to the positive and negative electrodes of the light emitter to be externally projected from the inside of the outer casing, and a first and a second means for protecting the light emitter from static electricity, the first means for protecting being the outer casing to which static electricity escapes, and the second means for protecting being static-electricity protecting means that is arranged between the positive and negative electrodes of the light emitter and prevents the static electricity from being applied to the light emitter; and
- an endoscope insertion portion comprising two terminals that electrically come into contact with the two terminals of the optical adaptor for endoscope, when being attached to the optical adaptor for endoscope, and wherein a cylindrical protecting member communicated with the inside and the outside of the outer casing is connected to the outer casing to be externally projected from the inside of the outer casing, and
- the two terminals are caved in the protecting member from a surface of the projected protecting member.

11. An endoscope apparatus according to claim 10, wherein the endoscope insertion portion comprises two terminals that electrically come into contact with the two terminals in the protecting member, caved in the protecting member, when being attached to the optical adaptor for endoscope.

12. An endoscope apparatus comprising:
- an optical adaptor for endoscope comprising, in an outer casing, the outer casing containing metal, at least one light emitter, having positive and negative electrodes, and serving as a light source for illumination, two terminals connected to the positive and negative electrodes of the light emitter to be externally projected from the inside of the outer casing, and a first and a second means for protecting the light emitter from static electricity, the first means for protecting being the outer casing to which static electricity escapes, and the second means for protecting being static-electricity protecting means that is arranged between the positive and negative electrodes of the light emitter and prevents the static electricity from being applied to the light emitter; and
- an endoscope insertion portion comprising two terminals that electrically come into contact with the two terminals of the optical adaptor for endoscope, when being attached to the optical adaptor for endoscope,
- wherein the static-electricity means of the optical adaptor for endoscope is a normally-closed switch, and
- wherein the endoscope insertion portion has, at its distal end, a projected portion that opens the normally-closed switch, when being attached to the optical adaptor for endoscope.

* * * * *